United States Patent [19]

Green et al.

[11] Patent Number: 5,304,187
[45] Date of Patent: Apr. 19, 1994

[54] SURGICAL ELEMENT DEPLOYMENT APPARATUS

[75] Inventors: David T. Green, Westport, Conn.; Boris Zvenyatsky, Bronx, N.Y.

[73] Assignee: United States Surgical Corporation, Norwalk, Conn.

[21] Appl. No.: 906,588

[22] Filed: Jun. 30, 1992

[51] Int. Cl.[5] .............................................. A61B 17/00
[52] U.S. Cl. ...................................... 606/151; 604/13; 604/15
[58] Field of Search ..................... 606/1, 151; 604/11, 604/13, 15, 60, 264, 286, 290

[56] References Cited

U.S. PATENT DOCUMENTS

| | | | |
|---|---|---|---|
| 636,637 | 11/1899 | Cooke | 604/13 |
| 700,139 | 5/1902 | Fuller | 604/13 |
| 702,997 | 6/1902 | Pugh | 604/13 |
| 2,524,195 | 10/1950 | Hoover | 604/13 |
| 3,918,452 | 11/1975 | Cornfeld | 604/11 |
| 4,769,038 | 9/1988 | Bendavid et al. | |
| 4,877,030 | 10/1989 | Beck et al. | |
| 4,986,831 | 1/1991 | King et al. | 606/151 |
| 5,007,895 | 4/1991 | Burnett | 604/11 |
| 5,059,211 | 10/1991 | Stack et al. | 606/211 |
| 5,064,435 | 11/1991 | Porter | |
| 5,074,840 | 12/1991 | Yoon | 604/11 |
| 5,116,357 | 5/1992 | Eberbach | 606/151 |
| 5,122,155 | 6/1992 | Eberbach | 606/151 |
| 5,147,374 | 9/1992 | Fernandez | 606/151 |
| 5,147,387 | 9/1992 | Jansen et al. | 623/1 |
| 5,176,692 | 1/1993 | Wilk et al. | 606/151 |

FOREIGN PATENT DOCUMENTS

WO92/06638  4/1992  PCT Int'l Appl.

OTHER PUBLICATIONS

Med Chem Products Endo-Avitene advertisement from the Jun. 1992 issue of *Surgical Laparoscopy & Endoscopy* Raven Press, Ltd.

Primary Examiner—Stephen C. Pellegrino
Assistant Examiner—Gary Jackson

[57] ABSTRACT

The present invention relates to an apparatus which facilitates endoscopic deployment and positioning of surgical elements adjacent to body tissue for subsequent securement thereto. The surgical element is wound within a tubular sleeve and then extruded from the distal end of the tubular sleeve. A method is also disclosed for deploying and positioning surgical elements using the apparatus of the present invention.

38 Claims, 10 Drawing Sheets

SURGICAL ELEMENT DEPLOYMENT APPARATUS

BACKGROUND OF THE INVENTION

1. Field of the Invention

The present invention relates to an apparatus and method for positioning surgical elements adjacent to body tissue. More particularly, this invention relates to an apparatus for winding surgical elements within an endoscopic tube for later positioning adjacent to herniated body tissue.

2. Description of the Related Art

Hernias are abnormal protrusions of an organ or other body structure through a defect or natural opening in a covering membrane, muscle or bone. An inguinal hernia is a protrusion which makes its way through the abdomen in the inguinal (groin) region. Hernias may be divided into three general classes: direct inguinal hernia, indirect inguinal hernia and femoral hernia. In both direct and indirect inguinal hernias, a part of the intestine may protrude through a defect (opening or tear) in the supporting abdominal wall to form a hernial sac. In a femoral hernia, a portion of the intestine is forced through the femoral ring into the femoral canal forming a hernial sac.

Traditional hernia repair surgery involves major invasive surgical procedures which often cause excessive trauma to the patient and necessitate long post-operative recuperative periods. The surgery typically requires an incision in the groin ranging up to six inches in length. Several layers of the abdominal wall are generally separated to reach the herniated portions. During the procedure, the opening or tear in the abdominal wall is closed in a manner which resembles the tying of a sack at the neck. Often a surgical mesh is attached by sutures directly over the repaired hernia opening to provide a reinforcement to the opening. In addition, numerous complications related directly or indirectly to the surgery often result including bleeding, infection, testicular atrophy, organ damage, nerve damage, blood vessel damage, etc. A detailed discussion of traditional hernia repair may be found in "Hernia Repair Without Disability, Second Edition", by Irving L. Lichtenstein. Such invasive surgical procedures are also utilized in other areas of the body, including surgery on the gall bladder, appendix, lungs and the like.

To avoid many of the previously stated risks and problems, the use of laparoscopic and endoscopic surgical procedures have become relatively popular and have provided additional incentive to develop the procedures further. In laparoscopic procedures, surgery is performed in the interior of the abdomen through small tubes inserted therein. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body should be substantially sealed to ensure that gases do not enter or exit the body through the incision. Moreover, laparoscopic and endoscopic procedures often require the surgeon to operate on organs, tissues and/or vessels far removed from the incision. Thus, instruments used in such procedures are typically long and narrow while being functionally controllable from a proximal end of the instrument.

In hernia surgery, as compared to gall bladder surgery, certain procedures and instruments are the same, and certain instrument requirements differ. For example, in hernia surgery a suitable mesh material is generally sutured over the opening in the tissue. Often, the mesh material is attached by sutures and left within the body to act as a reinforcing agent for tissue regrowth in the area of the surgery. One example of a mesh material currently utilized in hernia surgery includes a polypropylene material marketed by C. R. Bard, under the trademark MARLEX. Another example of a mesh material is a tri-fluoroethylene material marketed by W. L. Gore & Associates, Newark, Del., under the trademark GORE-TEX.

As noted, during conventional invasive surgical procedures, such mesh materials are manually placed over the defect in the abdominal wall and are often sutured within the surgical opening by conventional suturing techniques. However, with the advent of laparoscopic surgery the need for suitable mesh, mesh positioning and mesh attachment techniques through the relatively narrow tubes or cannulas is clearly defined.

Heretofore, resilient type mesh deploying apparatus have been provided which deploy a surgical implant from an endoscopic tube. An example of this type of mesh deployer is illustrated in *Surgical Laparoscopy & Endoscopy*, Vol. 1, No. 3, pgs. 151-153, which discloses an Endo-patch Spreader manufactured by Nanticoke Surgical Instruments Inc., Seaford, Del. However, such deploying apparatus are deployed by releasably securing the mesh to a spreader and simply disengaging the mesh from the spreader without further interaction between the mesh and the spreader. Thus, if a surgeon wants to further manipulate the mesh another instrument, such as a grasper, must be inserted into the surgical region.

Therefore, there remains a need for an apparatus which facilitates endoscopic deployment of surgical elements adjacent to body tissue within body cavities. Furthermore, there remains a need for facilitating endoscopic positioning of surgical implants adjacent to body tissue for subsequent securement thereto by means of sutures, clips, staples or the like.

SUMMARY OF THE INVENTION

The present invention relates to an apparatus for deploying surgical elements within body cavities, which apparatus comprises housing means, means for releasably maintaining a rolled surgical element within the housing means, and means for ejecting the surgical element from the housing means. Jaws are also provided which permit subsequent manipulation of the surgical element after deployment.

In addition to the above apparatus, the present invention relates to a method for positioning surgical elements adjacent to body tissue which comprises, releasably maintaining a surgical element within a tubular sleeve so that the surgical element is rolled within the tubular sleeve, positioning the tubular sleeve in close proximity to the body tissue, ejecting the rolled implant from a distal end of the tubular sleeve and manipulating the implant with the jaws such that the implant is positioned adjacent the body tissue.

3

BRIEF DESCRIPTION OF THE DRAWINGS

Preferred embodiments of the invention are described herein below with reference to the drawings wherein.

DETAILED DESCRIPTION OF THE PREFERRED EMBODIMENTS

In general, the object of the present invention is to endoscopically deploy and position surgical elements adjacent to body tissue. Surgical elements contemplated include implantable materials, such as surgical mesh, as well as non-implantable materials, such as sponges, gauze, hemostatic materials or the like. More particularly, the present invention relates to an apparatus for endoscopically deploying and positioning surgical implants adjacent to body tissue for subsequent securement thereto. However, the apparatus of the present invention may be adapted for conventional surgical procedures as well. Therefore, discussions relating to the proximal end of the apparatus or elements of the apparatus refer to the end closest to the surgeon. Similarly, the distal end of the apparatus or elements of the apparatus refers to the end furthest from the surgeon. Although the surgical implant will be discussed as a surgical mesh or a mesh implant, the surgical implant may be embodied in a wide variety of configurations. The use of the term "surgical mesh" or "mesh implant" is not intended to limit the types of implants which may be used in the present invention.

Figure 1:
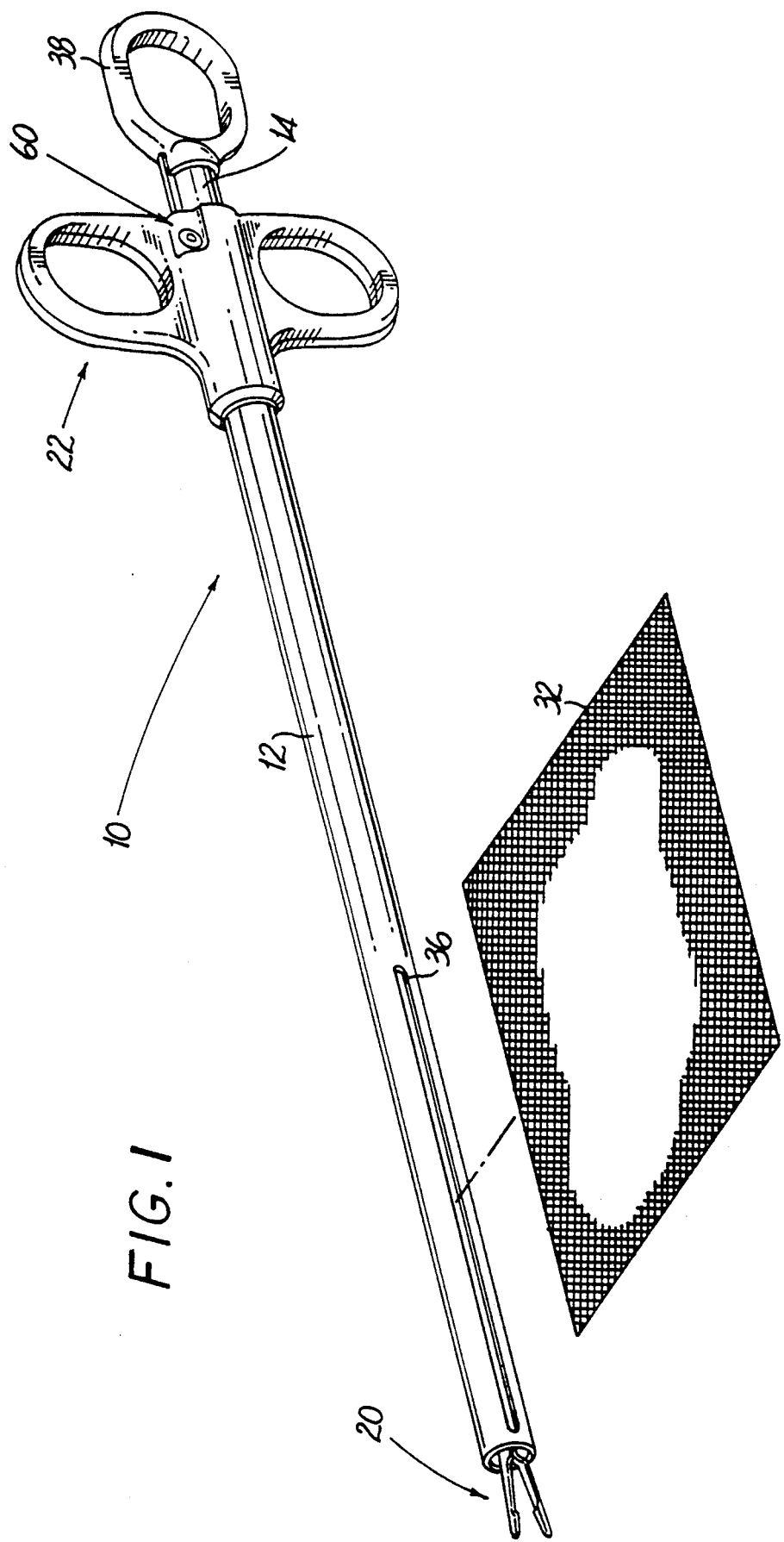
FIG. 1 is a perspective view of the preferred surgical mesh deploying apparatus of the present invention.
Figure 2:
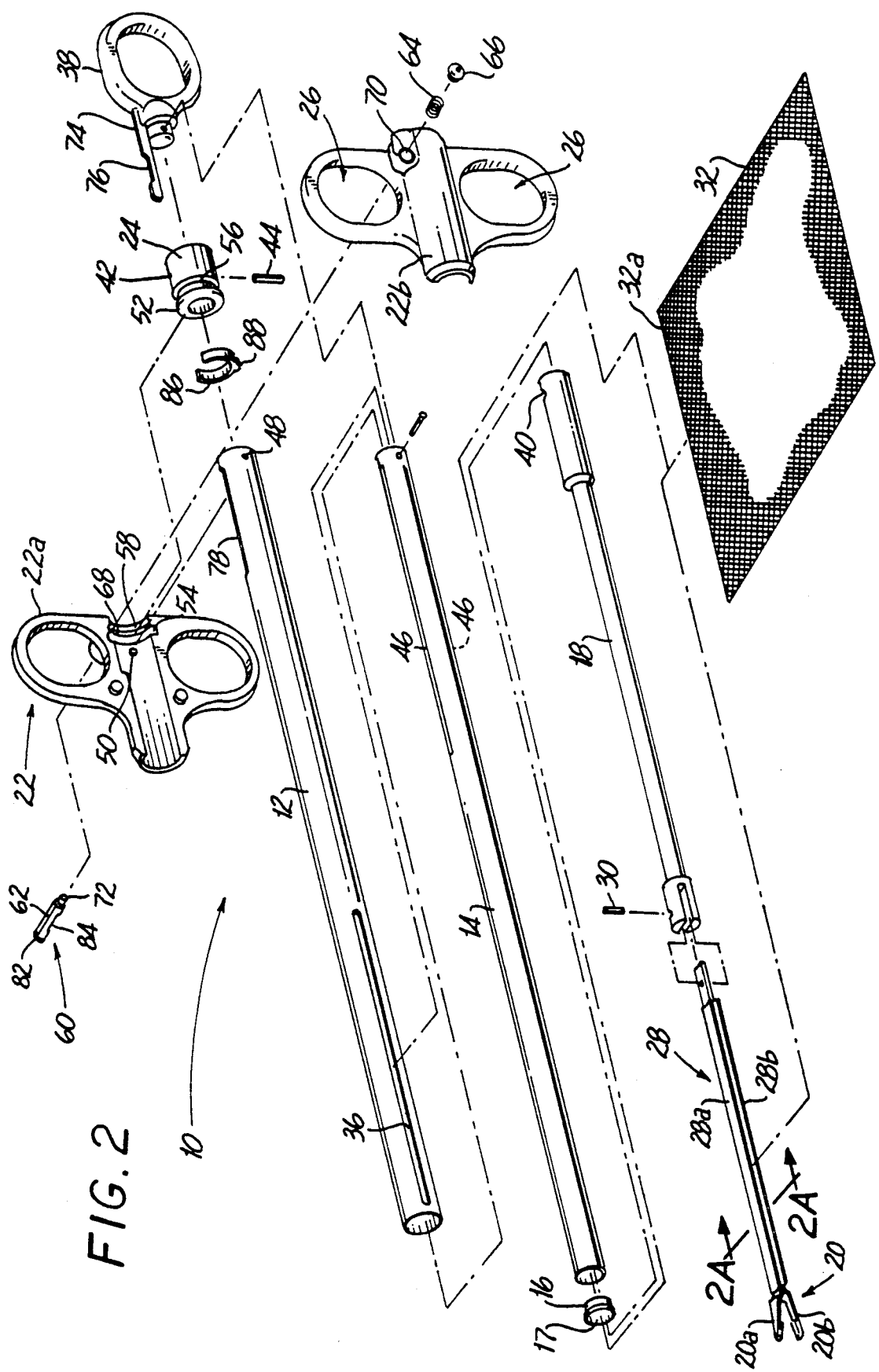
FIG. 2 is a perspective view with parts separated of the mesh deploying apparatus of FIG. 1, illustrating a clevis secured to the distal end of a mesh retainer which frictionally maintains a part of the surgical mesh.

Referring to FIGS. 1 and 2, the apparatus 10 of the present invention generally includes, tubular housing 12, pushing member 14 having a bushing 16 with camming surface 17 positioned at the distal end thereof and mesh retainer 18 having jaw assembly 20 positioned at the distal end thereof. In addition, the apparatus of the present invention may further include handle assembly 22, which may be of monolithic construction or constructed of separate pieces 22a and 22b secured together by ultrasonic welding, adhesives or the like. Collar 24 is rotatably secured to handle assembly 22 and is provided to rotate mesh retainer 18. Preferably, handle assembly 22 has eyelets 26 positioned therethrough which allow the surgeon to grasp handle assembly 22 with fingers and manipulate the mesh deployer. However, handle assembly 22 may be constructed in any configuration which facilitates manipulation of the mesh deployer.

Figure 2A:
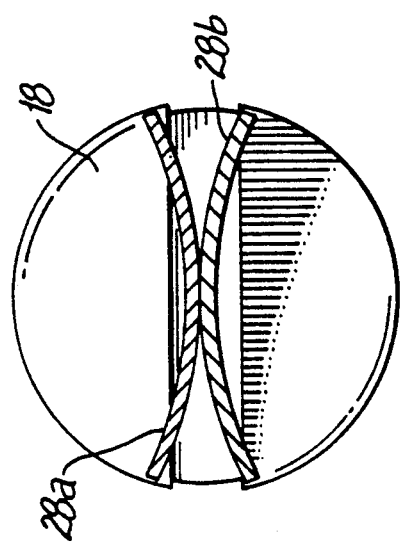
FIG. 2a is a cross-sectional end view of the clevis and mesh retainer taken along line 2a—2a of FIG. 2, illustrating the orientation of the clevis surfaces.

Referring to FIGS 2 and 2a, preferably the distal end of mesh retainer 18 has clevis 28 secured thereto by pin 30. Clevis 28 includes two opposing convex members 28a and 28b which meet at the center of each convex surface, as shown in FIG. 2a. This configuration allows clevis 28 to releasably and frictionally maintain one end (e.g., 32a) of mesh implant 32 within tubular housing 12 when mesh implant 32 is wound around clevis 28. In this preferred embodiment, jaw assembly 20 is formed or positioned at the distal end of clevis 28.

Figure 3:
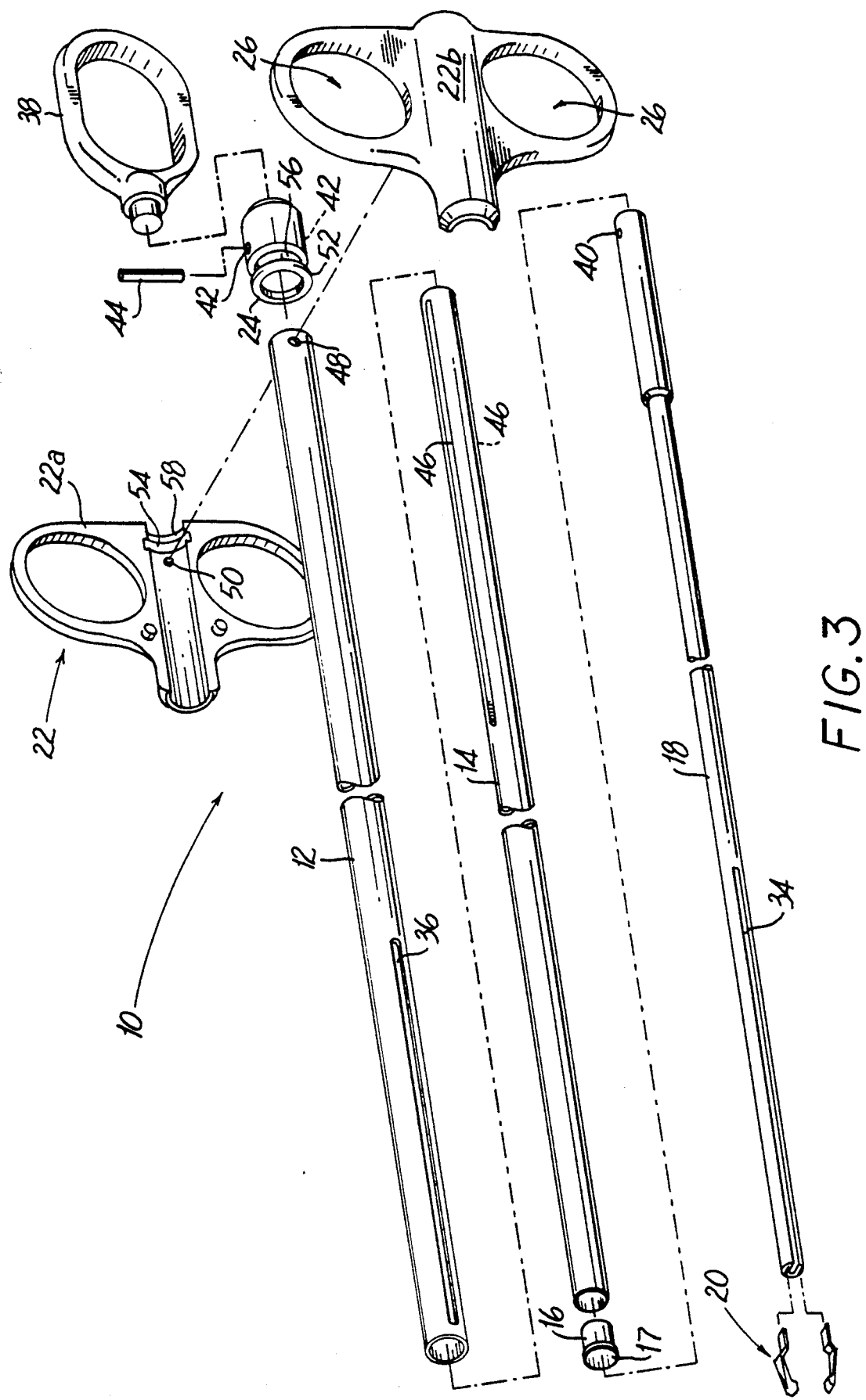
FIG. 3 is a perspective view with parts separated of an alternate embodiment of the mesh deploying apparatus of the present invention, illustrating a mesh retainer having a slot positioned at the distal end thereof for maintaining the surgical mesh.

In an alternate embodiment, shown in FIG. 3, mesh retainer 18 may simply be an elongated rod having elongated slot 34 positioned at the distal end thereof. Slot 34 receives mesh implant 32 and facilitates the winding of the mesh implant around mesh retainer 18 so as to releasably maintain mesh implant 32 within tubular housing 12. It should be understood that the function of slot 34 and clevis 28 are substantially similar, therefore, further discussions relating to slot 34 are intended to include clevis 28.

The relation of the orientation of tubular housing 12, pusher member 14 and mesh retainer 18 will now be discussed with reference to FIG. 3. Pusher member 14 is coaxially aligned within tubular housing 12 and collar 24 and is slidable between loading, unloaded and jaw moving positions. These positions of the apparatus are discussed in greater detail below.

Mesh retainer 18 is coaxially aligned within pusher member 14 such that mesh retainer aperture 40 aligns with collar apertures 42. In this configuration, pin 44 serves to mount collar 24 to mesh retainer 18. Pin 44 also extends through pusher member 14 via opposing elongated apertures 46 and allows proximal and distal movement of pusher member 14 without interference from pin 44. Rotational movement of collar 24 thus causes mesh retainer 18 and pusher member 14 to rotate within tubular housing 12.

As noted above, jaw assembly 20 is positioned at the distal end of clevis 28 (FIG. 2) or secured to the distal end of mesh retainer 18 (FIG. 3) so that jaws 20a and 20b are normally spaced apart. When pusher member 14 is in the jaw moving position, distal movement of pusher member 14 causes camming surface 17 of bushing 16 to cam against jaw assembly 20. As a result, the jaws are forced together thereby allowing the surgeon to grasp and manipulate the implant. Proximal movement of pusher member 14 reverses the camming action allowing jaws 20a and 20b to spring back to their original open state.

Referring again to FIG. 2, handle assembly 22 is secured to the proximal end of housing 12 so that apertures 48 positioned on opposing sides of tubular housing 12 engage protrusions 50 positioned on the interior wall of handles 22a and 22b. As noted above, collar 24 is rotatably secured to handle assembly 22. Annular ring 52 of collar 24 is maintained within channel 54 of each handle section 22a and 22b, while annular channel 56 of collar 24 engages flange 58 of each handle section 22a and 22b. This configuration secures collar 24 to handle assembly 22, as shown in FIG. 1 and allows rotational movement of collar 24 in relation to handle assembly 22.

Figure 4:
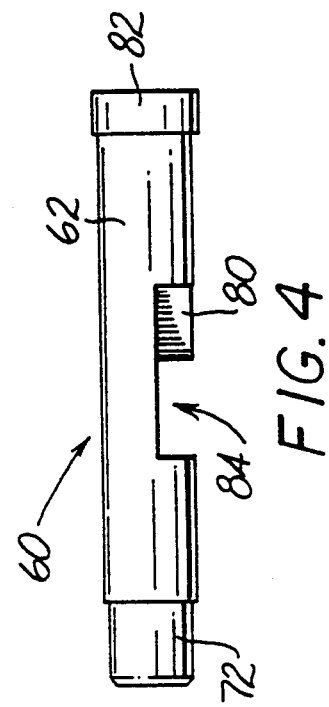
FIG. 4 is a side view of the locking assembly of the mesh deploying apparatus of FIG. 2.

In the preferred embodiment shown in FIGS. 2 and 4, handle assembly 22 includes blocking assembly 60 which restricts movement of pusher member 14 after deployment of the surgical implant. Blocking assembly 60 includes stop 62, spring 64 and cap 66. Stop 62 is positioned within aperture 68 of handle section 22a and extends into aperture 70 of handle section 22b. Spring 64 is positioned within aperture 70 so that stop 62 extends therethrough and cap 66 is secured to end 72 of stop 62. After deployment of the mesh by distal movement of loop 38, as will be discussed below, continued distal movement causes loop 38, which includes arm 74 and recess 76, to be further inserted into handle assembly 22 through collar 24 so that the distal end of arm 74 cams against the shaft of stop 62 enabling arm 74 to extend past stop 62 until stop 62 is positioned within recess 76. Slot 78 positioned at the proximal end of tubular housing 12 is provided to prevent interference between tubular housing 12 and arm 74. When pusher member 14 is in this position, recess 76 is in a substantially perpendicular relationship to stop 62 so that retractable pin 80 interferes with arm 74 and prevents substantial longitudinal movement of pusher member 14. However, minimal longitudinal movement is provided and is dependent upon the length of recess 76. Preferably, recess 76 is of sufficient length to allow pusher member 14 to open and close the jaws 20a and 20b of jaw assembly 20, as discussed above, thus limiting movement of pusher member 14.

To unlock pusher member 14 from the unloaded position, button 82 of stop 62 is manually moved towards handle assembly 22 thereby releasing retractable pin 80 so that channel 84 in stop 62 is aligned with arm 74. Once arm 74 and channel 84 are aligned, arm 74 may be manually withdrawn from handle assembly 22 by proximal movement of loop 38.

Figure 5:
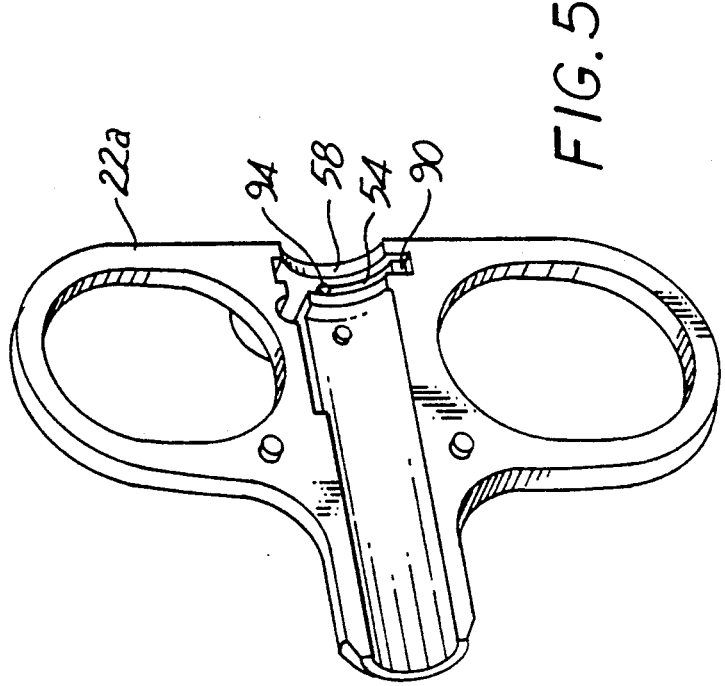
FIG. 5 is a perspective view of a part of the handle assembly of the mesh deploying apparatus of FIG. 2.
Figure 6:
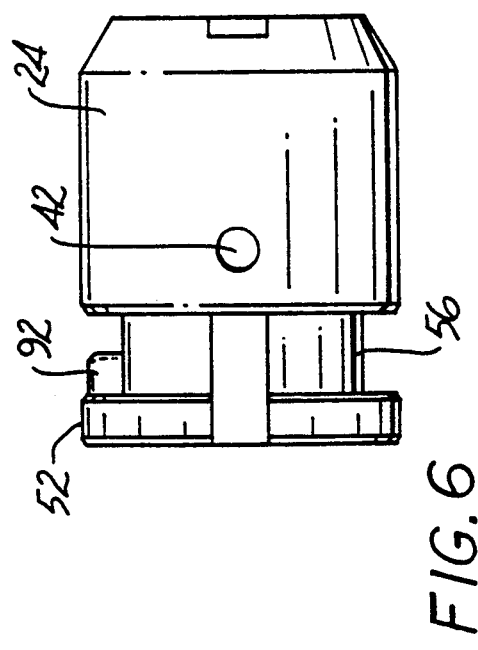
FIG. 6 is a side view of the collar of the mesh deploying apparatus of FIG. 2.

Turning to FIGS. 2, 5 and 6 indicators are provided to identify when mesh retainer 18 has been rotated a predetermined distance within tubular housing 12. Preferably, an audible indicator is provided to click after one revolution of mesh retainer 18. Audible indicator 86, preferably a wave spring washer, includes at least one nub 88 extending from the outer diameter thereof, as shown in FIG. 2. Audible indicator 86 is positioned within channel 54 of handle assembly 22 adjacent to the distal end of collar 24 such that nub 88 causes a friction fit between audible indicator 86 and channel 54. As shown in FIGS. 2 and 5, rotational movement of audible indicator 86 causes nub 88 to extend into indentation 90 of channel 54 thereby relaxing the friction force created by the friction fit so as to create an audible sound (i.e., a click). Although the preferred audible indicator provides for one click per revolution, numerous other configurations for the audible indicator may be provided. For example, audible indicator 86 may include multiple nubs positioned to indicate a quarter, a third or a half of a revolution.

A tactile indicator may also be provided which indicates when mesh retainer 18 has rotated within tubular housing 12 a predetermined distance, preferably one revolution. As shown in FIGS. 2, 5 and 6, collar 24 includes protrusion 92 extending into annular channel 56 of collar 24. As noted above, collar 24 is rotatably secured to handle assembly 22. The addition of protrusion 92 creates a friction fit between collar 24 and channel 54 of handle assembly 22. When protrusion 92 is aligned with indentation 94 associated with channel 54 of handle assembly 22, the friction force decreases to provide a tactile indication to the surgeon who is rotating the collar.

Figure 7:
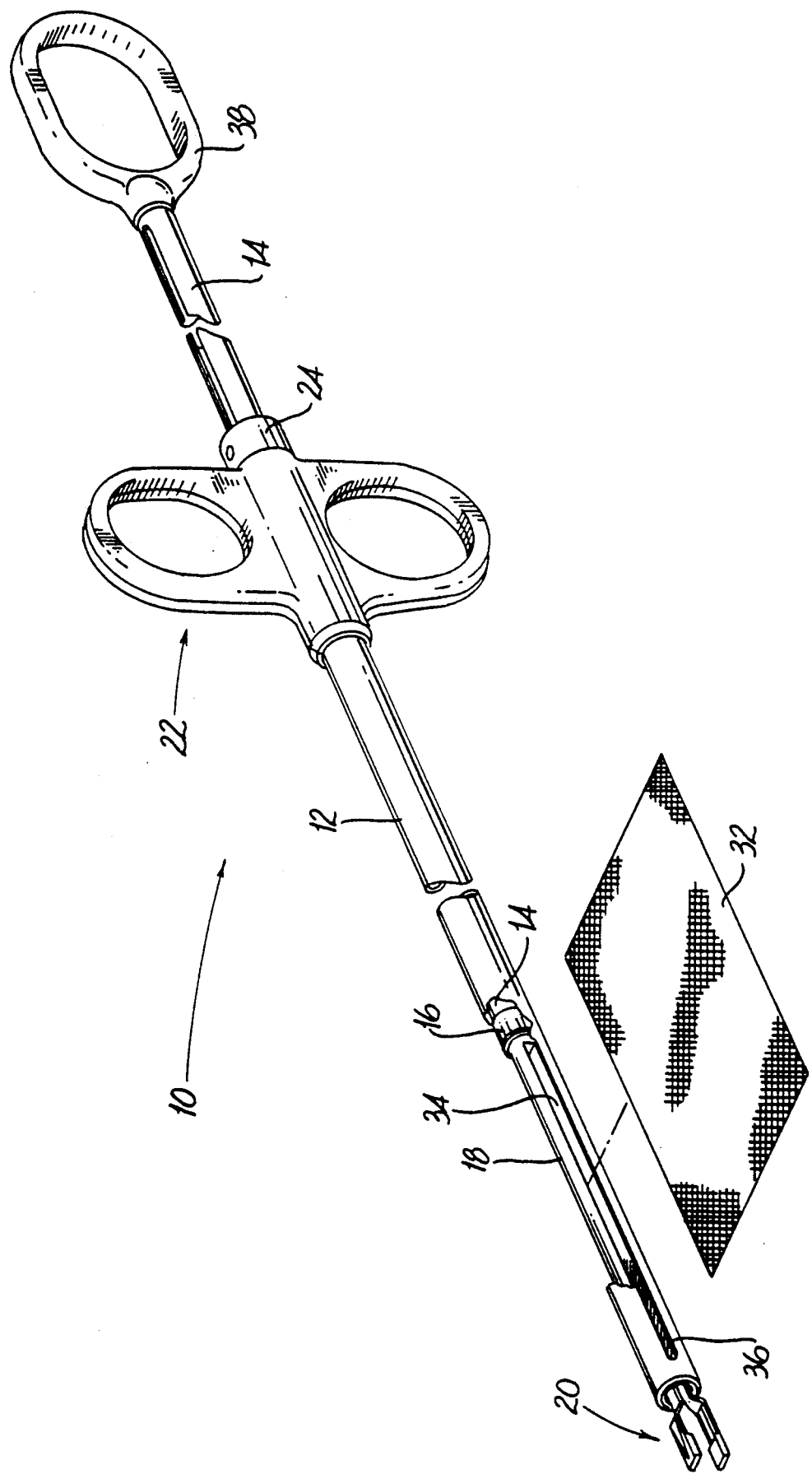
FIG. 7 is a perspective view in partial cut-away of the mesh deploying apparatus of FIG. 3, illustrating the mesh deploying apparatus in the loading position prior to rolling the mesh within the tubular housing.

Referring now to FIGS. 7 to 12, the operation of the apparatus will now be discussed. It should be noted that the operation of the apparatus of FIGS. 2 and 3 is substantially identical, therefore, for clarity the operation will be discussed with reference to the embodiment of FIG. 3 only. Initially, pusher member 14 is interposed between slot 34 of mesh retainer 18 and tubular housing opening 36 of tubular housing 12. To load the implant into the apparatus as shown in FIG. 7, pusher member 14 is retracted such that tubular housing opening 36 and slot 34 are in aligned communication. Surgical implant 32, preferably a mesh, is then inserted through housing opening 36 into engagement with slot 34. Although tubular housing 12 is shown in FIGS. 2 and 3 with a one tubular housing opening 36, tubular housing 12 may include numerous openings similar to opening 36. These openings may be radially positioned about tubular housing 12, so that alignment of any opening 36 with slot 34 will allow loading of surgical implant 32.

Figure 8:
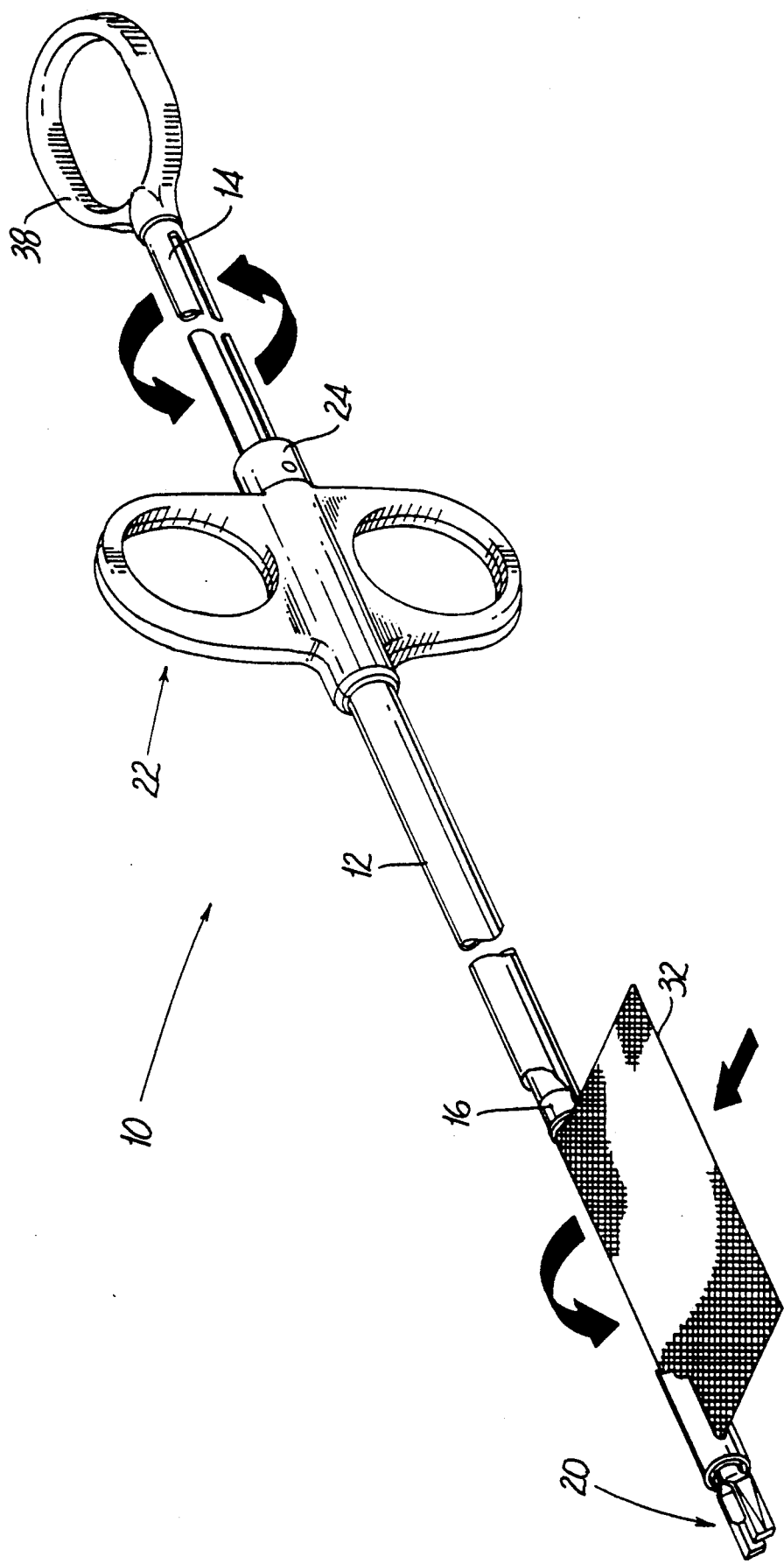
FIG. 8 is a perspective view in partial cut-away of the mesh deploying apparatus of FIG. 3, illustrating a surgical implant being rolled into the tubular housing.
Figure 9:
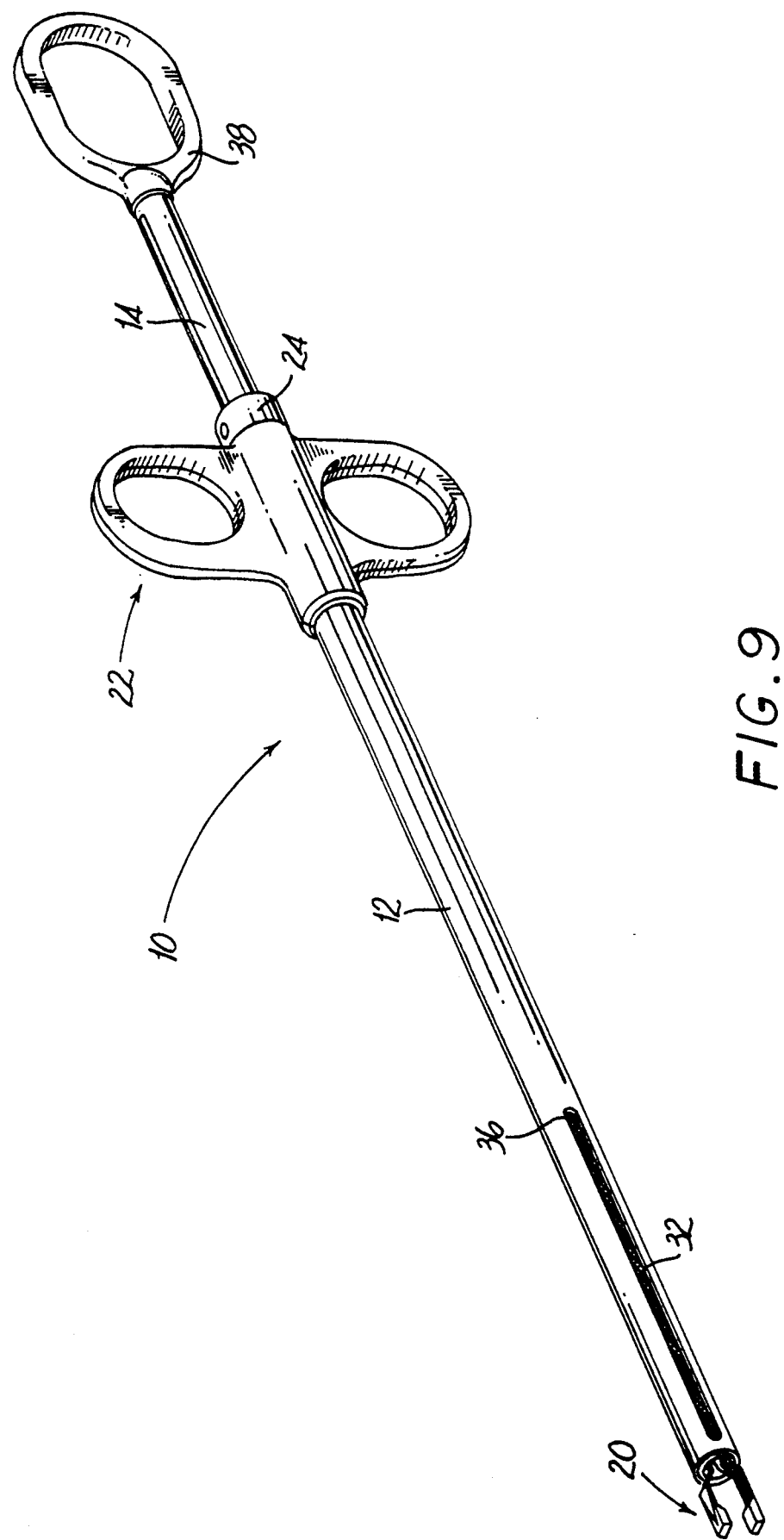
FIG. 9 is a perspective view of the surgical mesh deploying apparatus of FIG. 3 in the loading position having a mesh implant maintained therein.

As shown in FIGS. 8 and 9, mesh retainer 18 is rotated by turning collar 24 clockwise until mesh implant 32 is fully wound within tubular housing 12. As noted above, either the audible or tactile indicators may be utilized to verify when mesh implant 32 is fully wound within tubular housing 12.

Figure 10:
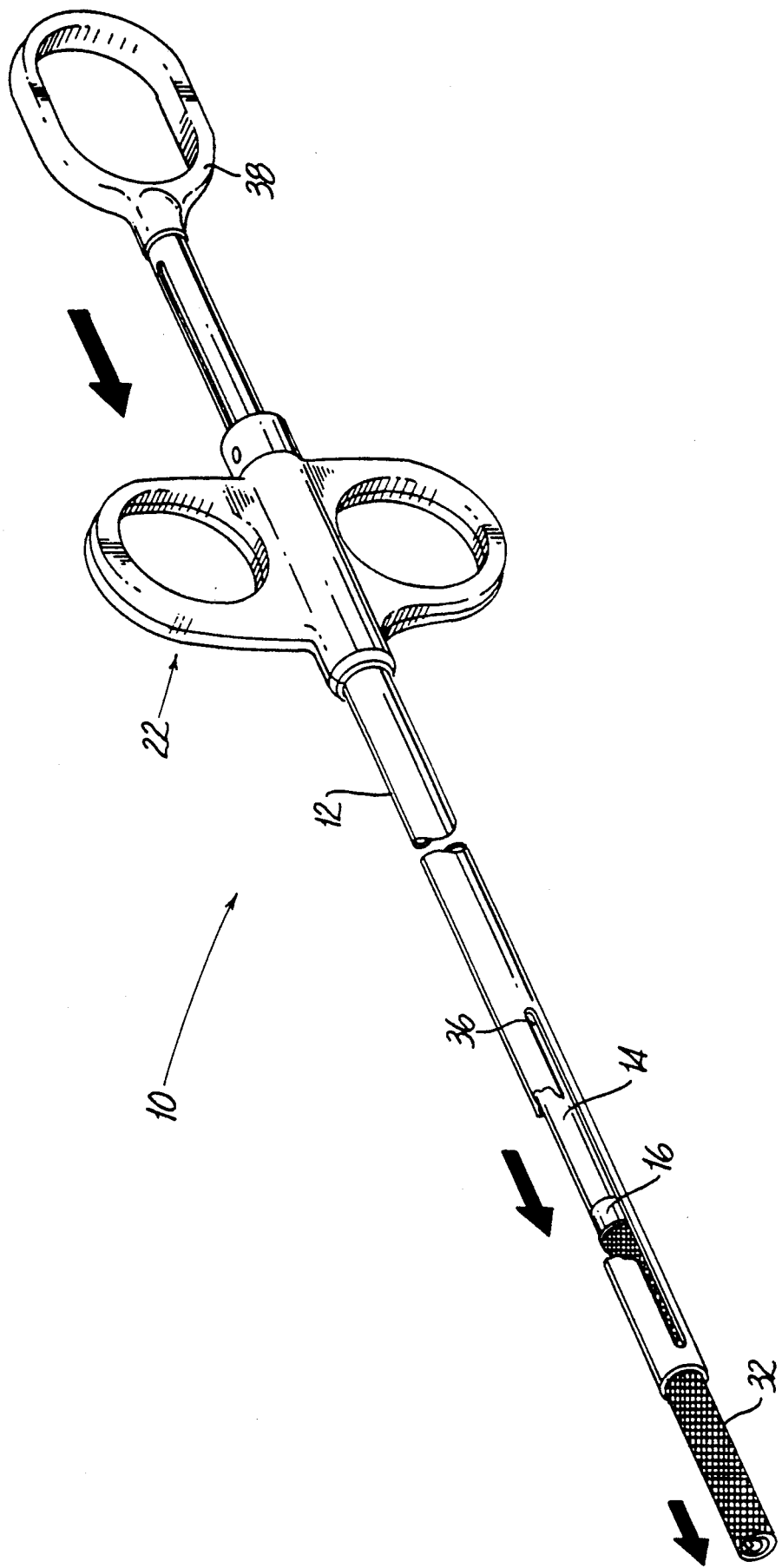
FIG. 10 is a perspective view in partial cut-away of the mesh deploying apparatus of FIG. 3, illustrating the surgical implant being deployed by the pushing member.
Figure 11:
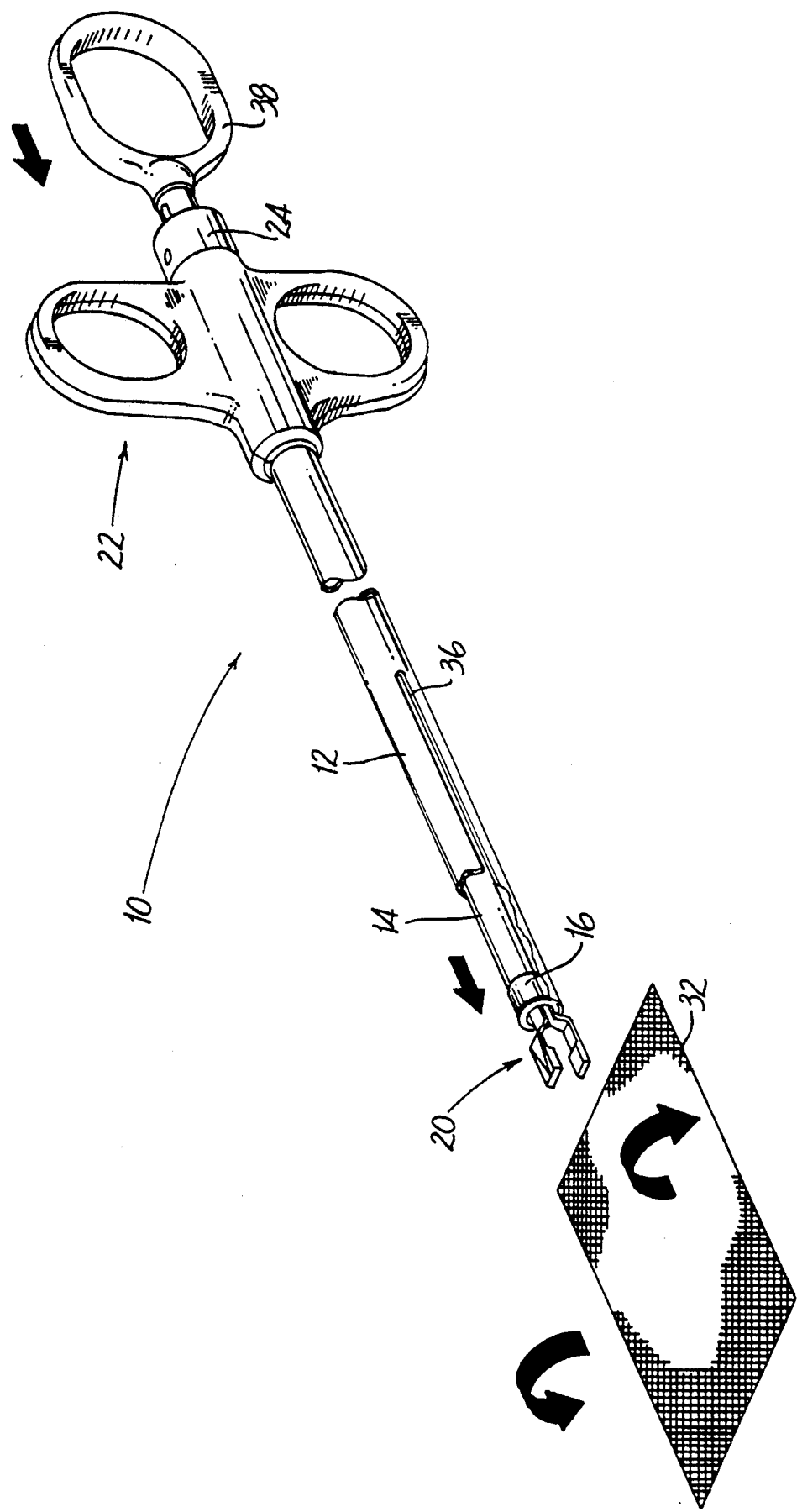
FIG. 11 is a perspective view in partial cut-away of the mesh deploying apparatus of FIG. 3, illustrating the mesh deploying apparatus in the unloaded position and the surgical implant unrolled after deployment.

To deploy the wound mesh implant, pusher member 14 is distally moved from the loading position to the unloaded position such that bushing 16 engages and ejects mesh implant 32 out of tubular housing 12, as shown in FIG. 10. Once exiting tubular housing 12, mesh implant 32 either automatically unrolls to a substantially flat state, shown in FIG. 11, or is manually unrolled by the surgeon using jaw assembly 20.

Figure 12:
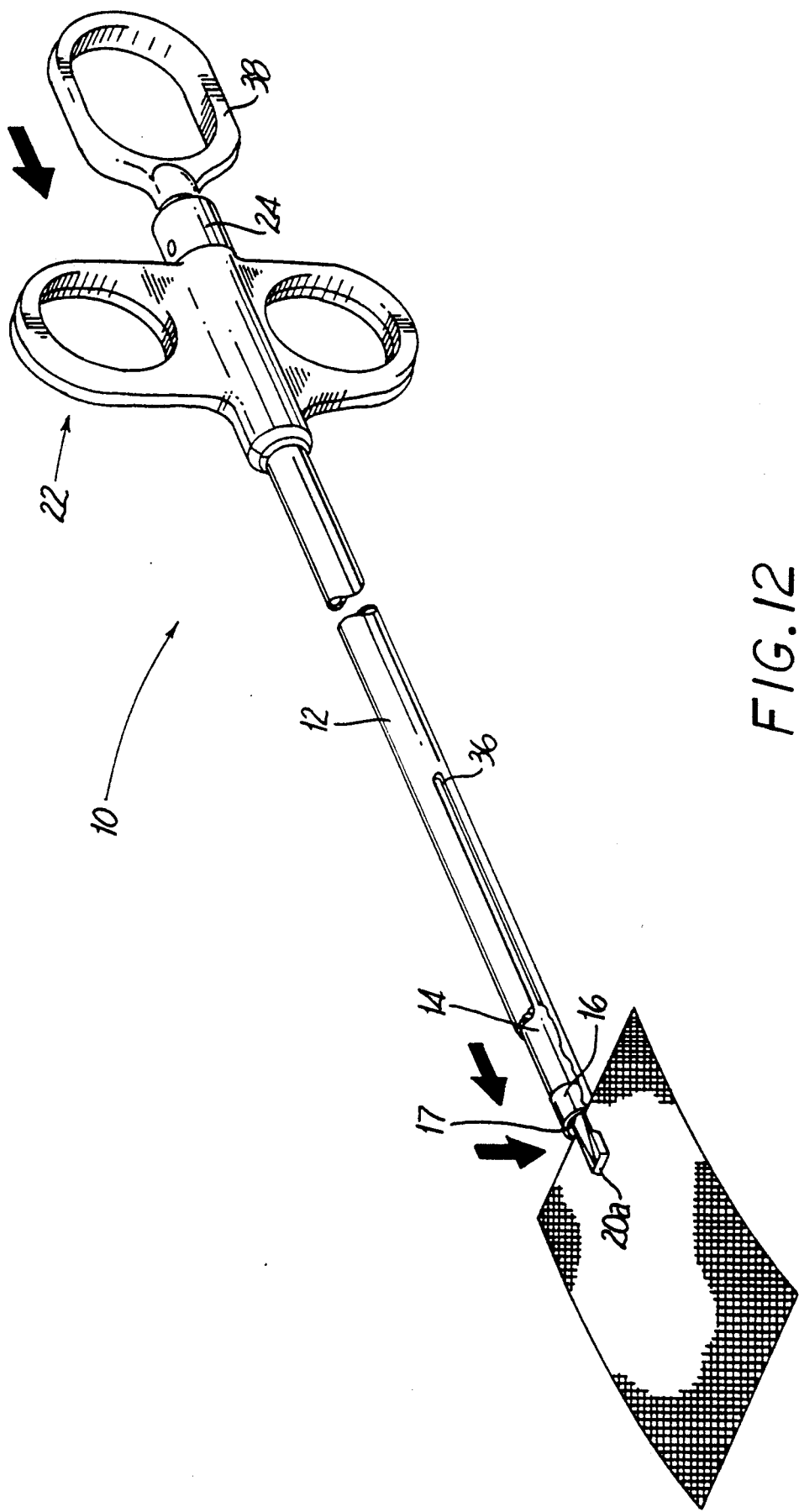
FIG. 12 is a perspective view in partial cut-away of the deploying apparatus of FIG. 3, illustrating the mesh deploying apparatus in the jaw closing position with the jaws grasping the surgical mesh.

Further manipulation of mesh implant 32 is accomplished by utilization of jaw assembly 20. As noted above, longitudinal movement of pusher member 14 to its distalmost position (i.e., the jaw moving position) causes camming surface 17 of bushing 16 to cam against jaws 20a and 20b of jaw assembly 20. This camming action causes jaws 20a and 20b to close, as shown in FIG. 12. Therefore, mesh implant 32 may be grasped by jaw assembly 20 and positioned within the body cavity without requiring the surgeon to insert other surgical instruments into the body cavity. Once mesh implant 32 is positioned adjacent the body tissue, the mesh may be secured thereto by means of sutures, clips, staples or the like.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention by merely as exemplifications of preferred embodiments thereof. Those skilled in the art will envision other modifications within the scope and spirit of the present invention as defined by the claims appended hereto.

What is claimed is:

1. An apparatus for deploying rolled surgical elements which comprises:
    housing means having a proximal end, a distal end and a longitudinal slot extending along at least a portion of an outer wall thereof, said housing means having a return member positioned therein to releasably receive a surgical element through said longitudinal slot and to releasably maintain the surgical element in a rolled configuration substantially within said housing means; and
    means at least partially positioned within said housing means for ejecting said surgical element from said distal end of said housing means.

2. The apparatus according to claim 1 further comprising manipulating means connected adjacent to said distal end of said housing means, said manipulating means being adapted for manipulating said surgical element after deployment from said housing means.

3. The apparatus according to claim 2, wherein said manipulating means comprises a pair of jaws.

4. An apparatus for deploying surgical elements which comprises:
    housing means having an elongated aperture longitudinally formed adjacent a distal end thereof;
    retaining means rotatably coaxially aligned within said housing means, said retaining means having an elongated channel longitudinally positioned adjacent a distal end thereof for releasably receiving at least a portion of a rolled surgical element within said channel;
    pusher means slidably aligned between said housing means and said retaining means for deploying the surgical element from said distal end of said housing means;
    jaw means positioned at said distal end of said retaining means such that said jaw means is extendable distally from said housing means and movable between open and closed positions; and
    means at least partially positioned within said housing means for moving said jaw means between said open and closed positions.

5. The apparatus according to claim 4 further comprising means for rotating said retaining means within said housing means.

6. The apparatus according to claim 4 further comprising:
    a handle secured to a proximal end of said housing means; and
    blocking means secured to said handle and adapted to releasably engage said pusher means for limiting movement of said pusher means.

7. The apparatus according to claim 4 further comprising indicator means operatively associated with said retaining means for indicating rotational movement of said retaining means.

8. The apparatus according to claim 7, wherein said indicator means comprises an audible indicator.

9. The apparatus according to claim 7, wherein said indicator means comprises a tactile indicator.

10. A surgical mesh deployment apparatus which comprises:
    tubular housing means having an elongated aperture longitudinally formed adjacent a distal end thereof;
    retaining means rotatably coaxially aligned within said tubular housing means, said retaining means having means for releasably frictionally securing a part of a rolled surgical mesh to said retaining means;
    pusher means slidably aligned between said tubular housing means and said retaining means for deploying the rolled surgical mesh from said distal end of said tubular housing means;
    jaw means positioned adjacent a distal end of said securing means such that said jaw means is extendable from said distal end of said housing means and movable between open and closed positions; and
    means at least partially positioned within said housing means for moving said jaw means between said open and closed positions.

11. The apparatus according to claim 10, wherein said securing means comprises a clevis.

12. The apparatus according to claim 10, wherein said moving means comprises a cam.

13. The apparatus according to claim 10 further comprising means for rotating said retaining means within said housing means.

14. The apparatus according to claim 13, wherein said rotating means comprises a collar operatively connected to a proximal end of said retaining means.

15. The apparatus according to claim 10 further comprising:
    a handle secured to a proximal end of said housing means; and
    blocking means secured to said handle and adapted to releasably engage said pusher means for limiting movement of said pusher means.

16. The apparatus according to claim 10 further comprising indicator means operatively associated with said retaining means for indicating rotational movement of said retaining means.

17. The apparatus according to claim 16, wherein said indicator means comprises an audible indicator.

18. The apparatus according to claim 16, wherein said indicator means comprises a tactile indicator.

19. A surgical mesh deployment apparatus which comprises:
    a housing having a handle portion and an endoscopic portion, said endoscopic portion having an elongated aperture longitudinally formed adjacent a distal end thereof;
    a mesh retainer rotatably coaxially aligned within said endoscopic portion of said housing, said mesh retainer having means for releasably frictionally securing a part of a rolled surgical mesh to said mesh retainer;
    a pusher member slidably aligned between said endoscopic portion of said housing and said mesh retainer for deploying the rolled surgical mesh from said distal end of said endoscopic portion;
    jaw means positioned adjacent a distal end of said securing means such that said jaw means are extendable from said distal end of said endoscopic portion of said housing and movable between open and closed positions;
    cam means positioned adjacent a distal end of said pusher member for moving said jaw means between said open and closed positions; and a rotating member rotatably secured to said handle portion and operatively connected to said mesh retainer for rotating said mesh retainer.

20. The apparatus according to claim 19 further comprising a blocking member secured to said handle portion of said housing and adapted to releasably engage said pusher member to limit movement of said pusher member.

21. The apparatus according to claim 19 further comprising a perceptible indicator associated with said mesh retainer for indicating rotational movement of said mesh retainer.

22. An apparatus for deploying surgical elements comprising:
    an elongated member having a proximal end and a distal end;
    means at least partially positioned within said elongated member for releasably retaining a surgical element therewithin; and
    a pair of jaws extending from and affixed to said distal end of said elongated member means for moving said jaws between open and closed positions for grasping the surgical element when deployed from said retaining means.

23. The apparatus according to claim 22 wherein said pair of jaws are movable between open and closed positions in response to cam means positioned adjacent a distal end of said retaining means.

24. The apparatus according to claim 22 further comprising pusher means positioned proximal to said surgical element for ejecting said surgical element from a distal end of said retaining means.

25. A method for deploying surgical elements adjacent to body tissue, comprising:
    receiving a surgical element within a tubular sleeve such that the surgical element is received through a longitudinal slot in said tubular sleeve so as to maintain the surgical element in a rolled configuration within said tubular sleeve;
    positioning said tubular sleeve in close proximity to the body tissue; and
    ejecting the rolled surgical element from a distal end of said tubular sleeve.

26. The method according to claim 25, wherein said surgical element comprises a surgical mesh implant.

27. A method for positioning a rolled surgical element adjacent to body tissue for subsequent securement thereto, comprising:
    providing a surgical element deployment apparatus having housing means with a longitudinal slot in an outer wall and configured to receive a surgical element through said longitudinal slot in said outer wall and configured to releasably maintain said surgical element substantially within said housing means so as to maintain said surgical element is a rolled configuration, and means for ejecting said rolled surgical element from said housing means;
    positioning said surgical element deployment apparatus in close proximity to the body tissue; and
    ejecting said rolled surgical element from a distal end of said housing means.

28. The method according to claim 27 further comprising manipulating said ejected surgical element such that said surgical element is positioned adjacent the body tissue.

29. The method according to claim 27, wherein said surgical element comprises a surgical implant.

30. The method according to claim 29, wherein said surgical implant is a mesh.

31. A method for repairing herniated body tissue comprising:
    providing a surgical element deployment apparatus for deploying a rolled surgical mesh, having housing means to releasably maintain said rolled surgical mesh substantially within said housing means, means for ejecting said rolled surgical mesh from said housing means and jaw means operable between open and closed positions, positioned at a distal end of said housing means;
    positioning said surgical element deployment apparatus in close proximity to the body tissue;
    ejecting the rolled surgical mesh from a distal end of said housing means;
    manipulating said ejected surgical mesh with said jaw means of said surgical element deployment apparatus such that said surgical mesh is positioned adjacent the herniated body tissue; and
    securing said surgical mesh to the body tissue.

32. An apparatus for deploying rolled surgical elements, which comprises:
    an outer tube;
    an inner rod rotatably positioned within said outer tube, said inner rod having means adapted to receive at least a portion of a surgical element and maintain the surgical element in a rolled configuration substantially within said outer tube; and
    a pusher member concentrically positioned between said outer tube and said inner rod, said pusher member being adapted to eject the surgical element from a distal end of said outer tube.

33. The apparatus according to claim 32, wherein said inner rod includes a pair of jaws extending from a distal end of said inner rod, said jaws being movable between open and closed positions.

34. The apparatus according to claim 32, wherein said portion of said inner rod adapted to receive the surgical element comprises a longitudinal slot configured and dimensioned to receive the surgical element.

35. The apparatus according to claim 34, wherein said longitudinal slot is configured and dimensioned to receive at least a portion of a substantially planar mesh implant.

36. A kit for deploying rolled surgical implants, which comprises:
    a surgical implant; and
    an apparatus for manipulating said surgical implant, said apparatus including an outer tube, an inner rod rotatably positioned within said outer tube, said inner rod having at least a portion thereof adapted to receive at least a portion of said surgical implant and to maintain said surgical implant in a rolled configuration substantially within said outer tube, and a pusher member concentrically positioned between said outer tube and said inner rod, said pusher member being adapted to eject said surgical implant from a distal end of said outer tube.

37. The kit according to claim 36, wherein said surgical implant comprises a mesh implant.

38. The kit according to claim 36, wherein said surgical implant comprises a substantially planar mesh implant.

* * * * *